(12) United States Patent
Kirn

(10) Patent No.: US 9,734,296 B2
(45) Date of Patent: Aug. 15, 2017

(54) ORTHOTIC SUPPORT AND STIMULUS SYSTEMS AND METHODS

(75) Inventor: Larry J. Kirn, Austin, TX (US)

(73) Assignee: Articulate Labs, Inc., Austin, TX (US)

( * ) Notice: Subject to any disclaimer, the term of this patent is extended or adjusted under 35 U.S.C. 154(b) by 363 days.

(21) Appl. No.: 13/878,586

(22) PCT Filed: Sep. 29, 2011

(86) PCT No.: PCT/US2011/054100
§ 371 (c)(1),
(2), (4) Date: Apr. 10, 2013

(87) PCT Pub. No.: WO2012/047737
PCT Pub. Date: Apr. 12, 2012

(65) Prior Publication Data
US 2013/0246036 A1    Sep. 19, 2013

Related U.S. Application Data

(60) Provisional application No. 61/387,968, filed on Sep. 29, 2010.

(51) Int. Cl.
*G06F 19/00* (2011.01)
*A61F 5/01* (2006.01)
*A61N 1/04* (2006.01)
*A61N 1/36* (2006.01)

(52) U.S. Cl.
CPC ........ *G06F 19/3437* (2013.01); *A61F 5/0123* (2013.01); *G06F 19/3481* (2013.01); *A61F 2005/0188* (2013.01); *A61N 1/0452* (2013.01); *A61N 1/36003* (2013.01)

(58) Field of Classification Search
CPC . A61F 5/0123; A61N 1/36003; A61N 1/0452; G06F 19/3437
See application file for complete search history.

(56) References Cited

U.S. PATENT DOCUMENTS

| 5,387,231 A * | 2/1995 | Sporer ............... A61N 1/36021 607/48 |
| 5,628,722 A | 5/1997 | Solomonow et al. |
| 6,002,859 A | 12/1999 | DiGioia, III et al. |
| 7,403,202 B1 | 7/2008 | Nash |
| 7,684,896 B2 | 3/2010 | Dariush |

(Continued)

FOREIGN PATENT DOCUMENTS

GB     2382777     6/2003

OTHER PUBLICATIONS

International Application No. PCT/US2012/054100, International Search Report dated Apr. 9, 2012.

(Continued)

*Primary Examiner* — Sean Dougherty
(74) *Attorney, Agent, or Firm* — Trop, Pruner & Hu, P.C.

(57) ABSTRACT

An embodiment of the invention includes (a) modeling a first internal force applied to a model of a user's joint based on a first external force externally applied to the joint at a first position; (b) modeling a second internal force applied to the model based on a second external force externally applied to the joint at a second position unequal to the first position; (c) comparing the first and second modeled internal forces; and (d) simulating the user based on the comparison. Other embodiments are described herein.

6 Claims, 7 Drawing Sheets

(56) References Cited

U.S. PATENT DOCUMENTS

| | | | | |
|---|---|---|---|---|
| 8,231,555 | B2* | 7/2012 | Skelton | A61M 5/14276 |
| | | | | 33/512 |
| 8,368,700 | B1* | 2/2013 | DiFrancesco et al. | 345/473 |
| 2003/0028220 | A1* | 2/2003 | Piraino | A61N 1/3906 |
| | | | | 607/7 |
| 2003/0074648 | A1 | 4/2003 | Brassard et al. | |
| 2003/0120183 | A1* | 6/2003 | Simmons | 600/595 |
| 2004/0044381 | A1* | 3/2004 | Duncan | A61N 1/36003 |
| | | | | 607/49 |
| 2004/0093093 | A1 | 5/2004 | Andrews | |
| 2005/0197814 | A1* | 9/2005 | Aram et al. | 703/11 |
| 2006/0058592 | A1* | 3/2006 | Bouma et al. | 600/301 |
| 2006/0167564 | A1* | 7/2006 | Flaherty | A61B 5/0476 |
| | | | | 623/57 |
| 2006/0206215 | A1 | 9/2006 | Clausen et al. | |
| 2006/0247904 | A1 | 11/2006 | Dariush | |
| 2007/0016329 | A1 | 1/2007 | Herr et al. | |
| 2008/0015827 | A1* | 1/2008 | Tryon et al. | 703/2 |
| 2008/0208287 | A1* | 8/2008 | Palermo | A61N 1/0452 |
| | | | | 607/48 |
| 2008/0288020 | A1 | 11/2008 | Einav et al. | |
| 2009/0183388 | A1 | 7/2009 | Miller et al. | |
| 2009/0326602 | A1* | 12/2009 | Glukhovsky | A61N 1/36007 |
| | | | | 607/41 |
| 2010/0004577 | A1 | 1/2010 | Yasuhara et al. | |
| 2010/0080428 | A1* | 4/2010 | Fontius | 382/128 |
| 2010/0303302 | A1* | 12/2010 | Kipman et al. | 382/107 |
| 2011/0208012 | A1* | 8/2011 | Gerber et al. | 600/300 |
| 2012/0310303 | A1* | 12/2012 | Popovic | A61N 1/36014 |
| | | | | 607/48 |
| 2013/0253607 | A1* | 9/2013 | Kirn | A61N 1/36003 |
| | | | | 607/48 |
| 2014/0148873 | A1* | 5/2014 | Kirn | A61N 1/20 |
| | | | | 607/49 |

OTHER PUBLICATIONS

International Application No. PCT/US2012/054100, Written Opinion of the International Search Authority dated Apr. 9, 2012.

State Intellectual Property Office of People's Republic China, First Office Action mailed Feb. 3, 2016 in Chinese Patent Application No. 201180057425.0.

European Patent Office, Extended European Search Report mailed Oct. 18, 2016, in European Patent Application No. 11831357.6.

* cited by examiner

| State | Identity and Values | Action |
|---|---|---|
| Safe (Default) | Medial Axial Force < 5% Lateral Axial Force < 5% | Cease Stimulation |
| Posterior Medial Tibia Protection | Medial Axial Force > 10% | Slow Onset of Stimulation proportional to Femur Sagittal Plane Position |
| Central Medial Protection | Medial Axial Force > 10% Lateral Axial Force > 10% | Stimulation proportional to Tibia Coronal Plane Position |
| Hyperextension Protection | Medial Axial Force > 5% | Rapid Maximal Stimulation |

Figure 4

ORTHOTIC SUPPORT AND STIMULUS SYSTEMS AND METHODS

CROSS-REFERENCE TO RELATED APPLICATIONS

This is a §371 application of PCT/US2011/054100, filed on Sep. 29, 2011 which claims benefit of provisional application Ser. No. 61/387,968, filed on Sep. 29, 2010, hereby expressly incorporated by reference herein.

BACKGROUND

Interfaces between biological and computing systems are becoming more commonplace, particularly in application areas of assistive rehabilitation and movement aids, such as powered prosthetic devices. The vast majority of these devices use state machine architectures, state definitions being comprised of one or more pre-defined pattern templates to translate between biological function and control algorithms. The state definitions used for these purposes, however, are necessarily idealized or averaged from a broad population. They therefore are invariably in any instance imperfect replicas of the underlying biological elements, which vary tremendously from individual to individual in differing conditions. Beyond these individual differences, environmental conditions, clothing, sensor positions, specific movements of an action, and motion speed are but a few of the many variables that can change extremely quickly, frustrating operation within any pattern template. To accommodate all variances, physical position and velocity patterns used must often then be so broad as to negatively impact even operation in slow-moving contexts. Further performance degradation in quickly-moving dynamic situations usually results when smaller positional changes, which occur more often at higher speeds, fall well within the broad template positional ranges mandated.

Adaptation of idealized state definition templates to an individual instance through selective parameter modification has shown moderate success, most notably improving transient behavior by tightening state boundary definitions. Even when dynamically optimized, however, direct comparison of measured conditions against any state definition template inherently limits viability to those conditions defined within the template. Inherently lacking extrapolation, predictable system control in a purely template-driven system occurs only when input conditions fall within template definitions. This therefore constrains tight control operation to circumstances in which the state definition templates have been either defined or trained. For example, dynamic adaptation which forms a template to define dynamically-stimulated leg muscle contraction criteria during normal walking on a level surface does not necessarily extend to previously unencountered situations, such as descending stairs. In the presence of poorly-defined states, direct measurement of the end control goal, particularly in biological applications, is therefore extremely difficult at best, making classic feedback loops untenable.

Following the leg stimulation example, the purpose of an orthopedic device may be to protect a damaged joint through external dynamically controlled force vectors. Implicit to this goal is maintaining internal vectored joint force magnitudes within proscribed limits. Due to inertial components in the multiple degrees of freedom involved, similar vectored forces within the joint may however result from a great number of disrelated positional and motion conditions. External position and motion measurements show poor correlation with internal vectored joint force magnitudes, primarily due to the compound nature of most joints. Direct control loop closure on internal joint forces is made untenable by joint invasion in most applications. For example, it may be impractical to calculate internal condyle forces by physically placing load cells inside the joint to get internal force measurements. Yet development of a positional template with high coverage of all scenarios requiring vectored joint protection is made unlikely by the sheer number of positions and motions possible. The previous example depicts a scenario wherein nonlinear behavior of a controlled system is not readily apparent through direct measurements, but is available in concise form through modeling of the physical system, as excited by measured dynamic conditions. This concise form is highly amenable to a state machine architecture, not only in biological interfaces like the example above, but in any control situation wherein direct control of higher-order effects of a multiplicity of excitation sources is desired.

Computational requirements of a state machine are in direct proportion to the number of state definitions inspected in any period of time. Highest efficiency then occurs with a minimum number of state exit/entrance criteria open for inspection at any given time. Significant control events, however, such as bone-on-bone condular impact in the orthopedic example above, often exist in a context of variances both in time and from instance to instance. In the example above, gait patterns predictive of condular impact vary significantly both with patient fatigue and from patient to patient. With broad physical system variances, identities of measured and even modeled conditions indicative of a significant control event can change or even be unknown when the control system is designed. Following the orthopedic example, knee kinematics are very different between heavy and slight patients. In this and many other examples, lack of extrapolative capability mandates that optimal state template definitions exhaustively cover possible system instances and conditions. A broad set of state condition criteria which covers all applications is not only computationally inefficient, but loses ability to distinguish by averaging the context in which significant control events are inspected.

A need exists for a state determination technique with adequate knowledge of the underlying structural system to allow robust and accurate control operation in both previously-observed and completely new operational conditions.

BRIEF DESCRIPTION OF THE DRAWINGS

Features and advantages of embodiments of the present invention will become apparent from the appended claims, the following detailed description of one or more example embodiments, and the corresponding figures, in which:

FIG. 4 includes state machine attributes of the architecture of FIG. 2 in the embodiment context of FIG. 3.

DETAILED DESCRIPTION

In the following description, numerous specific details are set forth but embodiments of the invention may be practiced without these specific details. Well-known circuits, structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact. Also, while similar or same numbers may be used to designate same or similar parts in different figures, doing so does not mean all figures including similar or same numbers constitute a single or same embodiment.

An embodiment includes incorporating one or more behavioral definitions of controlled structure with capacity to resolve dynamic responses of these definitions to measured dynamic conditions imposed on said structure into a controller utilizing a state machine architecture, and selectively including at least part of these dynamic responses into state entrance and/or exit criteria. Inclusion of structural definitions and their responses to stimuli therefore extends available state definition criteria to include calculated predictive or modeled response of the system under control. State discrimination is further improved through use of dynamic selection of parameters to be used for state entrance and/or exit criteria from this extended set of both measured and modeled information. Present and optionally historical streams of both measured and modeled parameters are provided to a discrimination algorithm which determines specific parameters to be used for optimal definition of two or more states. Stored state definitions so defined are compared to ongoing physical and modeled parameters to detect state recurrence, following conventional state machine practice.

Figure 1:
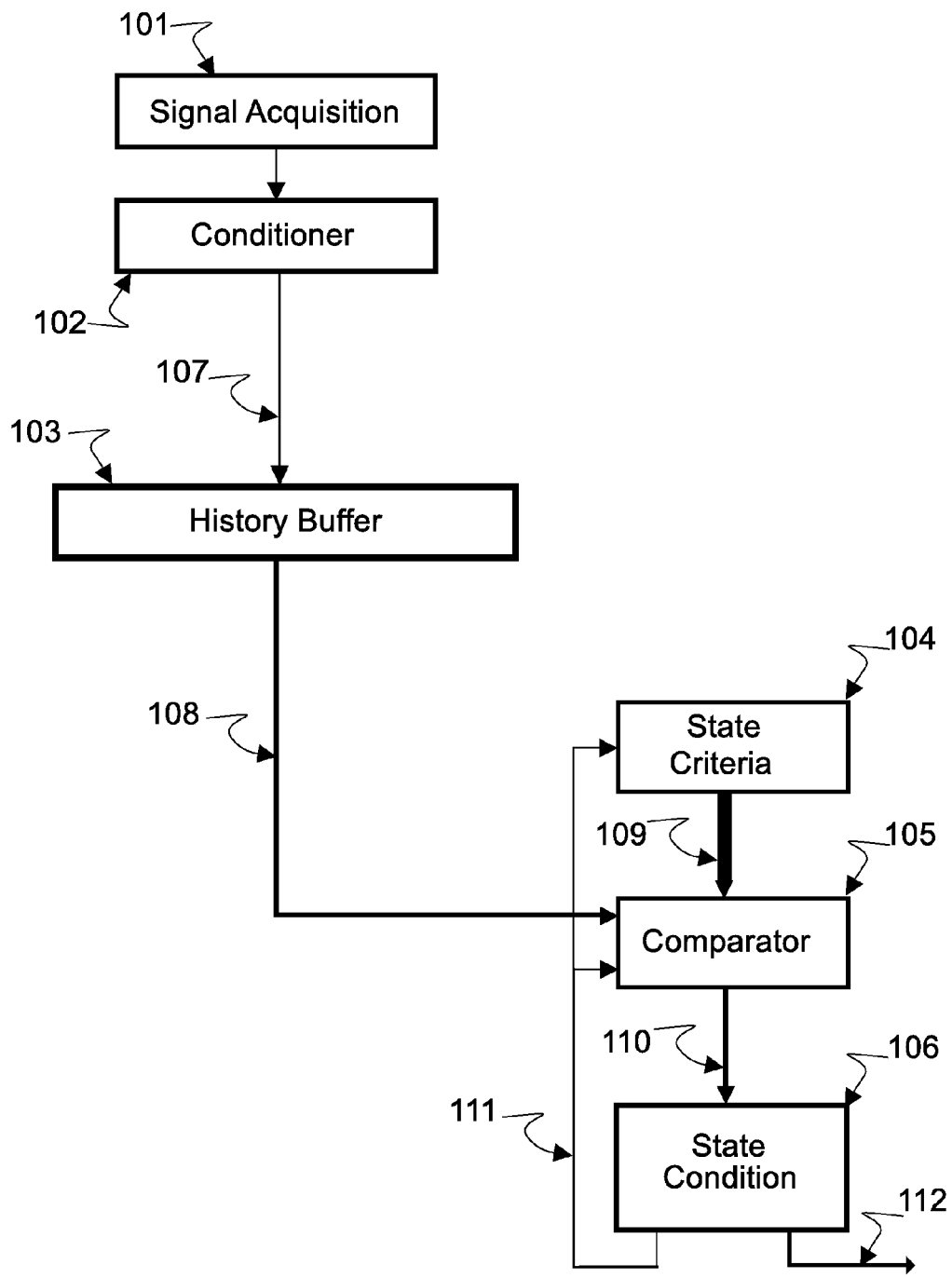
FIG. 1 includes a block diagram of a finite state machine controller.

Referring now to FIG. 1, Signal Acquisition 101 receives input from various sensors (e.g., via electrodes coupled to muscle) or metrics of the physical system to be controlled and performs data conversion into a form usable by the control system. Signal Conditioner 102 removes noise from incoming signals (e.g., via low pass, high pass, band pass filtering), limits bandwidth of each incoming signal, performs analog to digital conversion, and performs basic data conversions, such as integration and differentiation. Signals so processed by Conditioner 102 are provided at Parameter Stream 107 as input to History Buffer 103. History Buffer 103 provides at Parameter Stream 108 both current and historical renditions of signals of Parameter Stream 107. For example, Parameter Stream 108 may augment current measured and/or calculated information (e.g., positions, velocities, and accelerations) with historical renditions of the same information, which occurred 10 milliseconds (ms), 20 ms, 30 ms, 40 ms, and 50 ms ago. The addition of History Buffer 103 facilitates trend or trajectory calculations. For example, coupling generally instantaneous data with previous immediately preceding data helps determine acceleration vs. deceleration. Parameter Stream 108 is supplied as one input of Comparator 105.

State Criteria Buffer 104 is comprised of Sets of values (with identities of each) of one or more specific members of Data Stream 108 required for transition to a given system state. Each Set therefore specifies identities of, and finite value ranges of, one or more conditioned current or historical renditions of measured incoming system sensor information, coupled with indication of a specific system state. A state transition set appropriate for exit from the current system state is output as State Criteria Set 109, which is presented as a second input of Comparator 105, to be compared against Stream 108 discussed above.

Comparator 105 continuously monitors Parameter Stream 108 from History Buffer 103 to locate a value match in all identities of a State Definition output by State Criteria Buffer 104 (for the context of the Current State 111 discussed below) and the corresponding elements of Parameter Stream 108. Upon recognition of matching values between Parameter Stream 108 and State Criteria Set 109 currently output by State Criteria Buffer 104, Comparator 105 outputs the appropriate system State Transition Indication 110, optionally with parameters, indicated in the state definition to State Condition Buffer 106, which provides both current System State 111 and State Parameters 112 as outputs. State Transition Indication 110 therefore holds the current state and optionally parameters required of downstream control functions while in the current state of the state machine. System State Indication 111 is provided as a contextual input to Comparator 105. In that states available for entry are usually limited by the current state, State Indication 111 limits State Criteria Set 109, hence requisite comparisons by Comparator 105, to state exit/entry criteria appropriate to the current state only. System State 111 may optionally be supplied to application layer software. State Parameters 112, consisting of control constants such as gains or time constants appropriate to the current System State, are supplied to application layer software, which then presumably performs requisite activity (e.g., stimulation) for the denoted state.

Figure 2:
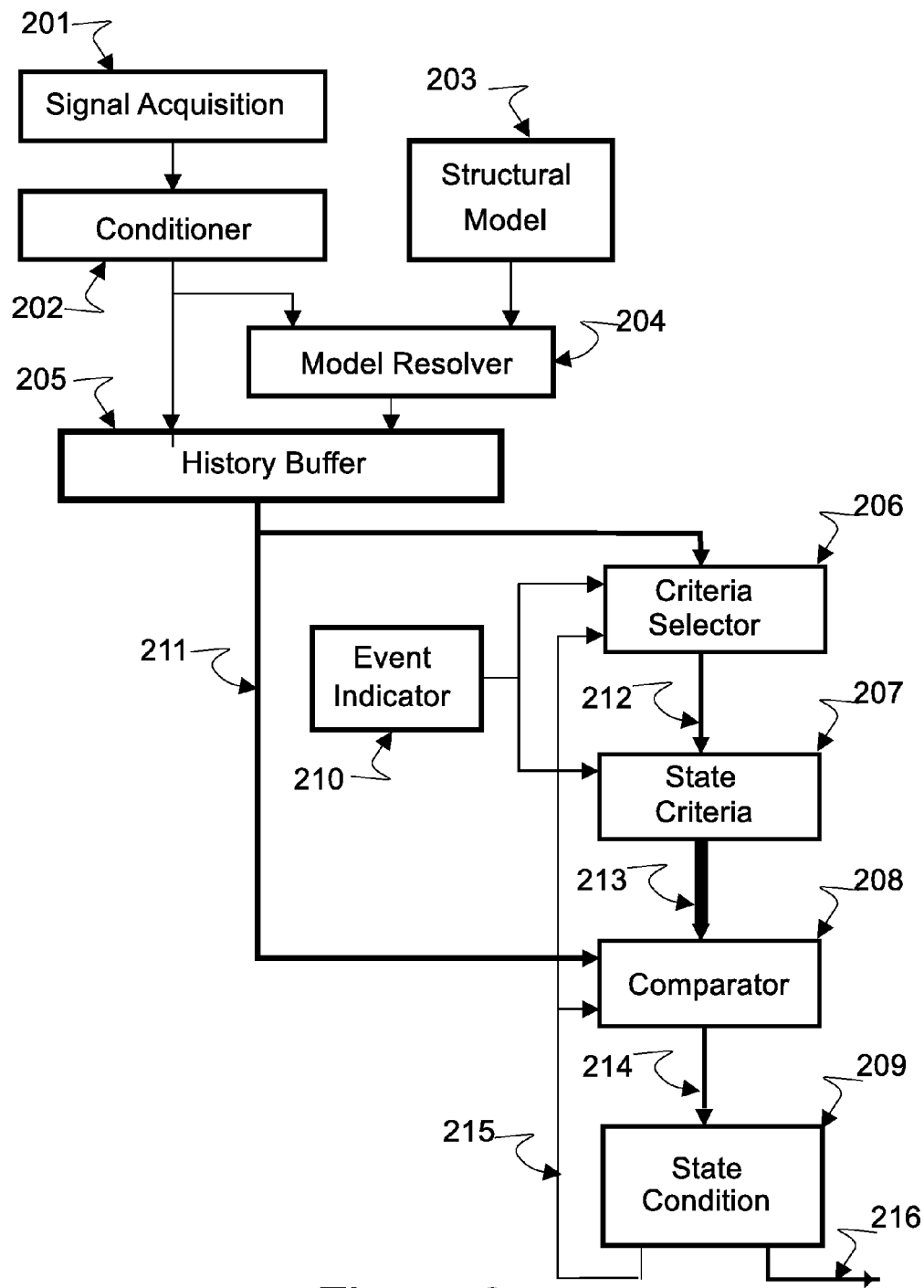
FIG. 2 includes a block diagram of a computational architecture demonstrating use of an embodiment of the invention.

Referring now to FIG. 2, Signal Acquisition 201, Conditioner 202, History Buffer 205, State Criteria Buffer 207, Comparator 208, and State Condition 209 perform the same functions of Signal Acquisition 101, Conditioner 102, History Buffer 103, State Criteria Buffer 104, Comparator 105, and State Condition 106, respectively, all of FIG. 1.

Structural Model 203 contains physical structural or response definitions of one or more underlying system elements, as stimulated with the same conditions measured by sensors input to Signal Acquisition 201. Examples of the output of Model 203 may be items such as number of elements, orientation, geometry, and compliances of the physical structure to be controlled. (Models are described further below in regards to FIG. 3.) Model Resolver 204, in response to both conditioned signals received from Conditioner 202 and definitions received from Structural Model 203, continuously calculates dynamic internal functional parameters of the underlying structure defined by Model 203, supplied as Modeled System Response to History Buffer 205. Examples of Modeled System Response may include relevant instantaneous vectored forces operable on each load-bearing element of the controlled structure. Specifically, the resolver may calculate how a combination of externally sensed conditions (e.g., data from accelerometers worn by the user) will translate into a specific internal force vector being applied to the lateral condyle.

History Buffer 205 then adds historical and current renditions of modeled system response from Model Resolver 204 to those being produced from Conditioner 202, at Parameter Stream 211. The addition of Structural Model 203 and Model Resolver 204 augments Parameter Stream 211 with modeled behavior of the physical system (e.g., knee joint, elbow joint) to be controlled. Note that current conditions and responses (delay=0) are provided as well as part of Parameter Stream 211, all elements of which are provided as input to both Criteria Selector 206 and Comparator 208.

Event Indicator 210 provides a trigger signal (e.g., from a user activating switch) at the occurrence of a significant unique operational event or condition (e.g., pain) requiring definition of a System State to both Criteria Selector 206 and State Criteria Buffer 207. The output of Event Indicator 210 may therefore be prompted by any set of signal conditions, including information from Parameter Stream 211. Specific parameters selected for monitoring by Event Indicator 210 may be partially or wholly determined by the current state of the state machine, System State 215, the source of which is to be described below. In addition to the output of Event Indicator 210, Criteria Selector 206 receives as input the Parameter Stream 211, and may as well optionally receive as input the current System State 215. Criteria Selector 206, upon receipt of a trigger signal from Event Indicator 210, determines both the identity and values of specific Parameter Stream 211 elements received from History Buffer 205 which will provide optimal state differentiation or behavior, within the context of the current (e.g. based on state condition 209) and optionally other system operating states. Examples of selection techniques used by Selector 206 may be peak signal derivatives, statistical prevalence, relative calculations between two or more input parameters, spectral deviation, and other signal discrimination methods. In an embodiment if the current state (e.g., based on state condition 209) indicates the knee is stationary then Criteria Selector 206 may choose to focus on, for example, peak signal derivative (e.g., rapid acceleration).

Selected parameter identities and values are provided as State Criteria Set 212 to State Criteria Buffer 207, which stores State Criteria Set 212 as a unitized State Definition at termination of the trigger signal from Event Indicator 210. State detection and resultant operation continues similarly to the system of FIG. 1, through activities of Comparator 208 and State Condition Buffer 209, as disclosed above, ultimately providing State Indication 215 and State Parameters 216.

The addition of Event Indicator 210 and Criteria Selector 206 represent improvements over conventional systems, introducing capability of the system to define its own future states, furthermore using data elements found by the control system itself to be optimal at the time of state definition.

Figure 3:
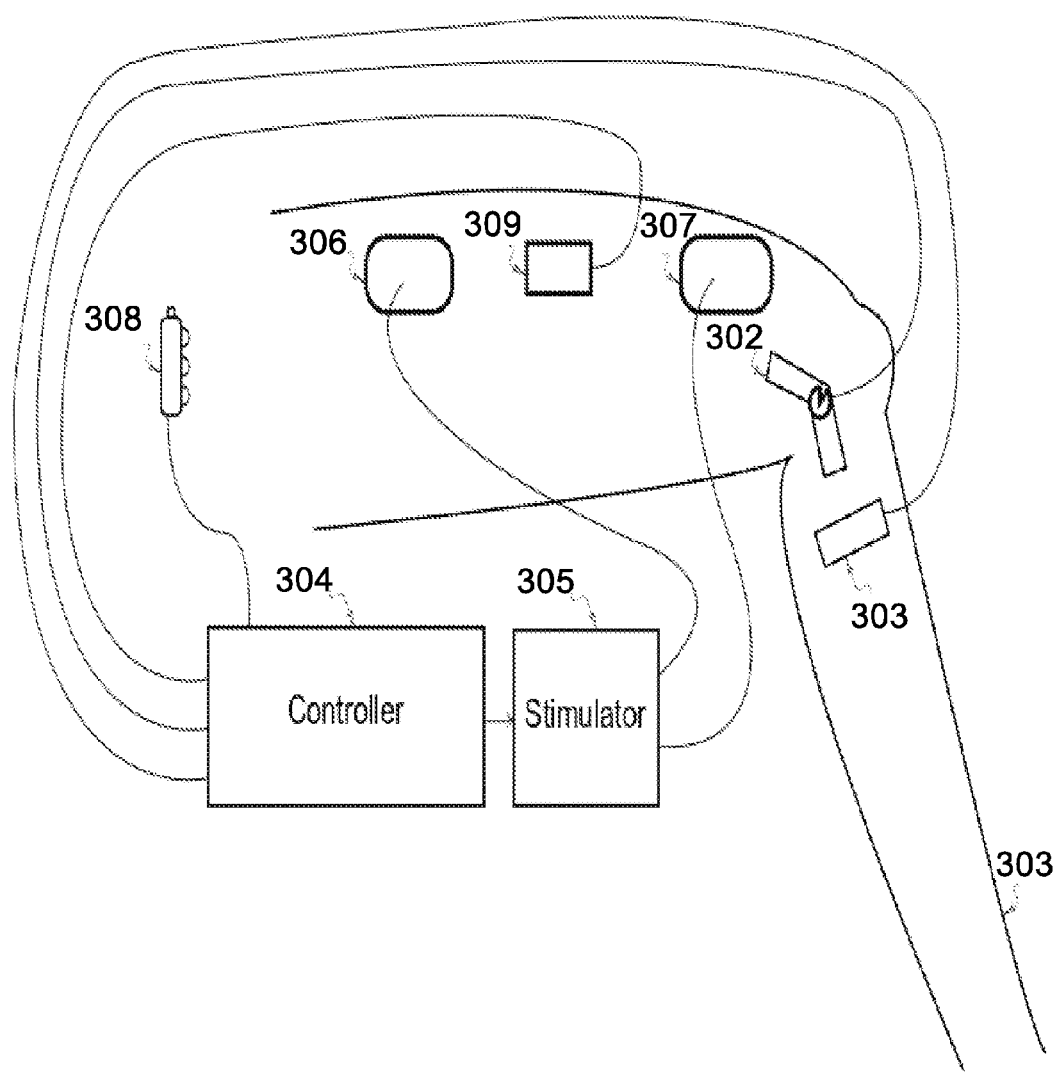
FIG. 3 includes a block diagram of an embodiment of the invention used to control an orthopedic muscle stimulation device affixed to a leg.

Referring now to FIG. 3, Accelerometers 303 and 309 are affixed to a human Leg 301. Positional Angular Sensor 302 is as well affixed to Leg 301, positioned at the center of knee rotation. Outputs of said sensors 302, 303, and 309 are supplied as input to Controller 304, which uses said sensor outputs to ascertain movements and function of Leg 301. It is assumed that said outputs of Accelerometers 303 and 309 each provide three independent information streams regarding X, Y, and Z-Axes. Controller 304 as well receives the output of Switch 308, which is used by the wearer to denote undesirable conditions such as pain.

Controller 304, under calculated conditions, outputs a control signal to Muscle Stimulator 305, which in response emits therapy (e.g., high-voltage pulses) to Electrodes 306 and 307 (e.g., transcutaneous electrodes). Said Electrodes 306 and 307 are attached to Leg 301 over the specific muscle from which additional joint support is desired. In response to said high-voltage pulses through Electrodes 306 and 307, the underlying muscle will contract to support the knee. The output of Controller 304 therefore indirectly controls additional knee support through elicited contraction of surrounding musculature.

In one embodiment, all functional blocks of FIG. 2 are embodied as hardware and/or software components of Controller 304 (with the exception of Event Indicator 210). At least part of the function of Event Indicator 210 of FIG. 2 is satisfied by Switch 308 of FIG. 3. It is presumed that Controller 304 incorporates a microcontroller capable of dynamically executing software instructions to effect dynamic elements shown in FIG. 2, but embodiments of the invention may use alternative computing means (e.g., masked application-specific integrated circuits). In an embodiment, the application layer of Controller 304 is comprised of multiple states (e.g., causing active or inactive outputs to Stimulator 305).

In operation, outputs of Sensors 302, 303, and 309 are acquired into acceptable form by Signal Acquisition 201 of FIG. 2. Output of Signal Acquisition 201 is filtered and additionally converted into, for example, integral and derivative forms by Conditioner 202 of FIG. 2. The output of said Conditioner 202 therefore will therefore confer knee position and motion derived from Sensor 302, as well as both static (gravitic) position and dynamic motion of both femur and tibia of Leg 301, derived from Sensors 309 and 303, respectively. A structural model of the knee is stored in permanent memory of Controller 304 (see block 203 of FIG. 2). Said structural model may contain finite element definitions as simple as two frictionless ball joints of specific physical spacing, or as complex as four condylar surfaces with intermediary compliance gradients of meniscus, joint laxity, and synovial fluid.

In conjunction with said output of Conditioner 202 of FIG. 2, these model definitions are applied to a Model Resolver 204, also of FIG. 2. The output of said Resolver provides modeled force magnitude and vectors for internal forces present on the two condyles of the knee. For example, given that gravity and body mass of a given user are both relatively constant, accelerations (including gravitic force) in three orthogonal axes of two connected body members can be used to approximate forces applied to internal elements of a joint connecting the two body members. Vectored static forces on each joint element are a function of angular position of each body member, relative to the earth. Vectored dynamic forces on each joint element are comprised of differential accelerations of the relatively constant masses of the two body members as connected to a central body mass, and common-mode accelerations of primarily the central body mass. Relative vectored forces may be used for force modeling in the given application area and absolute forces are not strictly necessary in on embodiment of the invention.

Output from module 204 is supplied as input, along with the output of Conditioner 202, to History Buffer 205, also of FIG. 2. Following the previous example, History Buffer 205 would then as well provide into Stream 211 current renditions of modeled calculations such as medial and lateral condyle vectored forces, as well as these same vectored forces 10 ms, 20 ms, 30 ms, 40 ms, and 50 ms ago. Under control of the state machine structure described herein, Controller 304 provides one or more parameters as input to Stimulator 305, hence controlling application of muscle stimulation pulses to Electrodes 306 and 307. An embodiment describing what happens after history buffer 205 is described further below.

In day-to-day operation, the patient wearing the system of FIG. 3 will perform motions during which additional muscle support for pain mitigation is necessary, and press Switch 308 when pain or other undesirable conditions exist (which can be mitigated indirectly through muscular stimulation). Subsequent activities by the wearer, which create conditions similar to those marked undesirable by Switch 308 activation, will result in neuromuscular stimulation output to Electrodes 306 and 307 to mitigate pain and/or damage from future activities. In contrast, conventional methods use external force only (e.g., with no application from the external force to an internal force applied to a model) or deviation from idealized gait templates. Each and every condition or motion requiring stimulation must be memorized in order to achieve this end. Many of these conditions or motions, however, are hazardous to the wearer.

When visualized in normal activities, it will be seen that various force vectors will be applied to various parts of the knee of Leg 301. Deeper inspection will reveal that multiple dissimilar activities of Leg 301 may create very similar vectored forces internal to similar parts of the knee. For example, rapid forward movement of Leg 301 will create knee forces similar to those created by placing weight on the leg while extended behind the body; yet position and movement measurements obtained from Sensors 302, 303, and 309 will be dramatically different for these two activities. Relying upon measured information (e.g., external position sensors worn on outside of leg) without knowledge of the underlying structure (i.e., no modeling of internal knee joint) may mandate that Switch 308 be activated during each and every problematic activity in order to achieve the desired purpose of the exemplary device. This presents a large number of activities during which the device must be trained many of which may impose user danger and which must later be differentiated upon during system use.

Assuming that knee pain or damage may be predicted by impending or present vectored force magnitudes, Structural Model 203 of FIG. 2 may be comprised of representations of structural knee elements necessary to resolve internal vectored knee forces when excited by the position and motion information of Signal Conditioner 202 of FIG. 2. This model resolution then decouples resultant internal vectored forces from external position and motion measurements, accommodating the circumstance that any given vectored internal force may be precipitated by a multitude of position/movement combinations. Internal vectored knee forces in this example are therefore a much better analog to specific knee pains than are position or motion indications. Even though potentially caused by very dissimilar activities or motions, problematic vectored knee forces can be readily identified by excitation of an accurate model, greatly reducing state definition complexity.

Individual statures, gait differences, and pathologies create an extremely broad operating range for the exemplary system of FIG. 3. Although indication of pain through Switch 308 activation serves to highlight a set of conditions during which muscle stimulation is desired, functional discrimination is still severely diluted by the common practice of using of a large fixed subset of conditions to be inspected for state determination. In any given operational condition, very few measured and/or modeled conditions serve to unequivocally delineate a desired protection state, while many other measured and/or modeled conditions provide inconsequential noise only. Given wide use-to-use variance, such as seen in patient-to-patient gait differences, specific identities of salient information to be used for state inspection is often known only as the system is in actual use, not during the design cycle. For example, compression of the medial condyle is not readily discriminated from compression of the lateral condyle, if many knee positions, movements, and forces are inspected for state detection in the system of FIG. 3. In the case of medial compression, however, force on that condyle indicated by model output, as shown above, exhibits a high deviation from its statistical average; while modeled lateral condyle force remains near its statistical average. For this application, therefore, inspection of those elements within Parameter Stream 211 of FIG. 2 with the highest rate of change serves to enhance discrimination immensely. This follows the circumstance that laxity in an arthritic knee causes force on a damaged condyle to begin suddenly, as the condyle collapses under load. Smooth force changes (with resultant low derivatives) are much less problematic than abrupt force changes (high derivative).

In an embodiment, following this implementation Criteria Selector 206 of FIG. 2 then identifies incoming elements of Stream 211 with the highest derivative values, while Switch 308 of FIG. 3 is pressed (see also block 210 of FIG. 2), for inclusion in the appropriate State Definition to be stored in State Criteria Buffer 207 of FIG. 2. In another embodiment, the selection algorithm in use by Criteria Selector 206 may consist of detecting those elements of Stream 211 with the highest statistical prevalence, as observed during multiple activations of Switch 308 of FIG. 3. Another embodiment would serve to reduce the effect of instantaneous timing errors through averaging.

In contrast to the use of static data identities for state determination in convention systems, inclusion of Event Indicator 210 and Criteria Selector 206, both of FIG. 2, in an embodiment of the invention shows identification during actual use of those data elements most indicative of the event denoted by activation of Switch 308, of FIG. 3. Although readily discerned during use, specific identities best suited for state identification may or may not be known at the time the control system is designed.

Detection of data elements with highest derivative values or statistical prevalence during Switch 308 activations, and subsequent use of these similar vectored forces by Criteria Selector 206 of FIG. 2 to define States requiring muscle support creates, per discussion above, State Definitions in State Criteria Buffer 207 reflective of undesired vectored knee forces, regardless of the precipitating motions. When these vectored knee forces within Stream 211 are again detected by Comparator 208, State Transition 214 therefore causes State Condition Buffer 209 to provide constants to downstream control software indicative of the appropriate protective state. Presumably, constants presented to the downstream control system by State Condition Buffer 209 for the detected state of problematic knee force will cause or intensify muscle stimulation from Stimulator 305 of FIG. 3, mitigating undesired results of the force. Future motions which create vectored knee forces learned to be problematic in State Criteria Buffer 207 will therefore result in protective activity by the exemplary device, even though motion causing the problematic vectored force may never have existed during activation of Switch 308 of FIG. 3.

In an embodiment Controller 204 utilizes adaptive techniques to functionally normalize all inputs on an ongoing basis and perform error/noise correction. This is necessary to compensate the expected variances of environment, fatigue, etc., so as to prevent Criteria Selector bias from sensor gain differences. Following the previous example of using maximal condylar force derivative for state detection, sensor manufacturing tolerances could, in the absence of normalization, cause a static condylar bias reflecting sensor gain error, rather than condylar differential.

Referring now to FIG. 4, State Description, Criteria Identities and Values, and ultimate Control Action are shown for five exemplary states of the architecture of FIG. 2, as applied to the embodiment of FIG. 3.

State Descriptions for each state shown are solely for explanatory purpose; transition to each exemplary state, as indicated by State Transition 214, may be affected by token, handle, number, and the like. In an embodiment, entities with a highest rate of change (following the stated example) are chosen by Criteria Selector 206 for use in State Definitions to be stored in State Criteria Buffer 207. Criteria Identities and Values show results to be expected (although not in any way mandated) from Criteria Selector 206 at receipt of a trigger from Event Indicator 210. Actions shown for each state are anticipated Stimulator 305 outputs resultant of State Parameters 216, applied to control software downstream of the current invention. In an embodiment the stimulation amplitude ultimately provided is a function of calculated force on the medial condyle, and the lateral vastus is stimulated by Electrodes 306 and 307.

As shown, the Safe (default) State is entered from any active state whenever the most active condylar force is below 5% of full scale. Stimulation is ceased, presumably through low gains presented at State Parameters 216.

The Posterior Medial Tibia Protection State could be expected to originate from a user pressing Switch 308 while ascending a single stair, placing stress on that portion of the knee. In the (typical) circumstance of medial erosion, sudden medial (modeled) force above 10% could be expected. In active users, rapid deceleration of the femur (giving a high derivative) could additionally be expected, so could be as well selected by Criteria Selector 206. Gradually-increasing stimulation would be expected, reflective of the causal motion.

The Centered Medial Protection State could be expected as the user enters stance phase of the gait cycle by planting the heel of Leg 301. High force derivatives could be expected on both condyles, usually accompanied by high tibial accelerations in the transverse plane. In the example shown, higher force on the lateral (sound) condyle is used to qualify the lower force on the medial condyle. In a user with a more rapid gait, however, it could be expected that Criteria Selector 206 would find a greater derivative in tibia transverse plane motion. Thus, one embodiment uses that information as well for state determination. Sudden onset of stimulation would be expected.

The Hyperextension Protection State could be expected in a user with a cruciate ligament injury, just prior to heel strike. Highest change could be expected in modeled ligament force (included in the knee model), although knee rotation could create high coronal plane acceleration of the femur with high joint laxity. Brevity of the resultant knee force would produce rapid, pronounced stimulation.

It can be seen that the number of states shown will depend upon the number of conditions found painful by the user, and that addition, and modification, of states may be effected through use of Switch 308. It is assumed that state erasure may be accomplished through a separate activation of Switch 308, causing Event Indicator to delete unwanted states as they occur.

Figure 5:
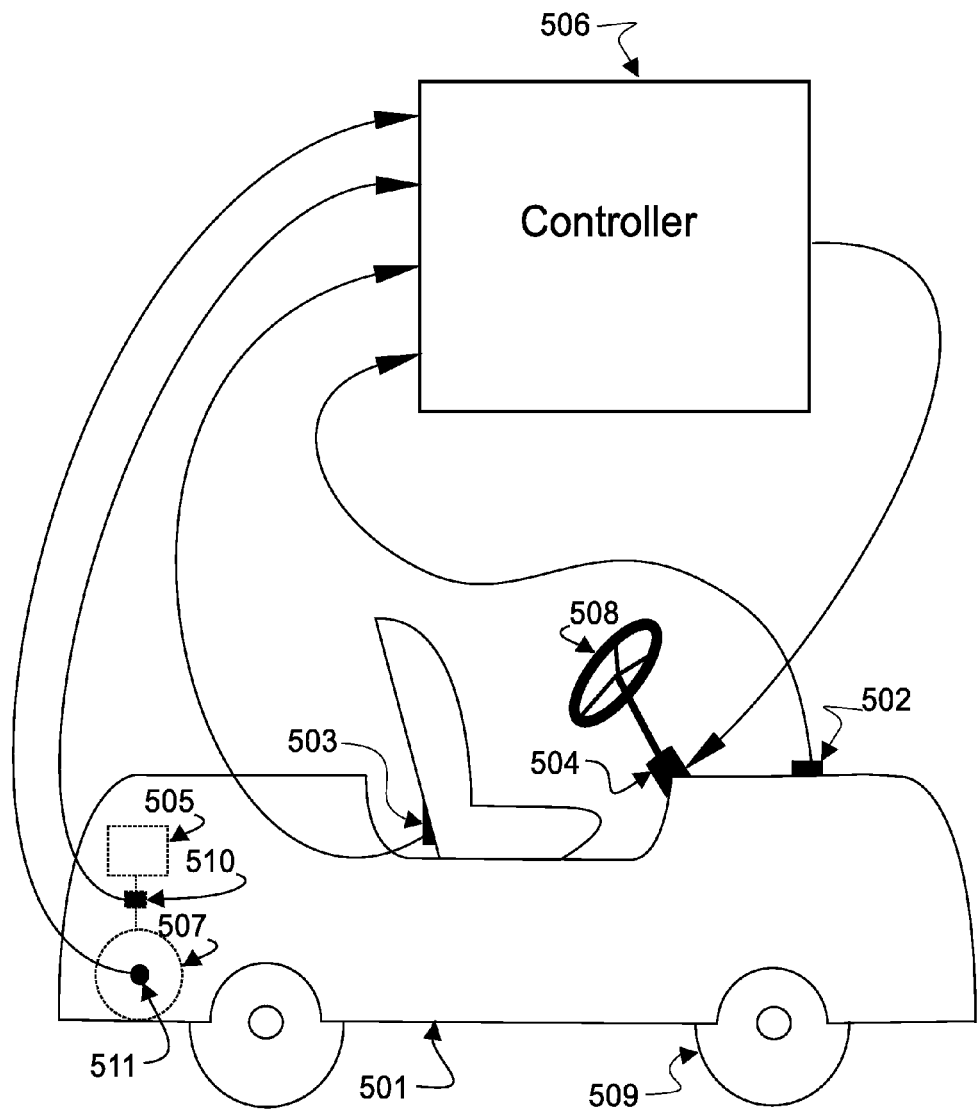
FIG. 5 includes a block diagram of an embodiment of the invention used to improve stability of a golf cart.

Referring now to FIG. 5, Three-Axis Accelerometer 503 is placed at the nominal center of gravity of Golf Cart 501. GPS Sensor 502 is affixed to an area of Golf Cart 502 with optimal view of positioning satellites. Battery 505 provides power to electric Motor 507 through Current Monitor 510. Speed Sensor 511 is attached to the output shaft of Motor 507, hence indicating axial speed of said Golf Cart 501. Variable-Ratio Drive 504, presumably an electrically-driven planetary gear arrangement, modifies the angular movement of front Wheels 509 caused for a given rotation of Steering Wheel 508. Controller 506 receives input from said Accelerometer 503, GPS Receiver 502, Speed Sensor 511, and Current Monitor 510; and provides variable control to Variable-Ratio Drive 504, modulating the steering ratio of Golf Cart 501.

Golf carts are notorious for poor lateral stability, yet their prime use is on hilly terrain. An embodiment of the invention reduces the likelihood of cart roll-over through modulating the steering ratio of the vehicle.

Accelerometer 503, GPS Receiver 503, Speed Sensor 511, and Current Monitor 510 provide input to Signal Acquisition 201 of FIG. 2, which performs the activities given in its description above. Structural Model 203 contains an elevation map of the golf course on which Golf Cart 501 is to be operated, presumably in a coordinate system compatible with GPS Receiver 502. Controller 506 contains an embodiment of the current invention, as shown in FIG. 2, that context following:

Model Resolver 204 applies current physical location and heading, inclination in three axes, and vehicle speed from said Inputs 502, 503, and 511, respectively, to the terrain map of Structural Model 203 in order to resolve maximum safe yaw rate of change for any given set of circumstances. Maximum safe yaw rate so calculated is included with conditioned inputs denoted above as input to History Buffer 205. Event Indicator 210 provides a signal to Criteria Selector 206 and optionally State Criteria 207 at each significant increase of vehicle speed. Upon receipt of said signal, Criteria Selector selects one or more of vehicle speed, vehicle acceleration, or vehicle inclination as the most probable cause of rollover for the given circumstances, and creates two State Definitions in State Criteria 207. The first State Definition is one of several States indicating relative probability of rollover, noting that the golf cart can roll over even at extremely low speeds if tilted far enough. The second State Definition indicates conditions under which steering ratio is to be decreased in order to prolong stability.

Comparator 208 monitors incoming Stream 211 against at least the two State Definitions illustrated in the preceding paragraph, updating current State Indication 214 as necessary to State Condition 209. State Condition 209 provides constants to downstream control software including a base safe steering ratio during the first State Definition above, and one or more constants denoting limits above which steering ratio is to be reduced during the second State Definition above. Upon receipt of said constants, downstream control software directly controls the steering ratio of Variable-Ratio Drive 504, of FIG. 5.

At the onset of forward motion, a base steering ratio will be applied, decreasing with inherent risk of current vehicle conditions, as indicated by the specific State chosen for said first State Definition. This is to improve predictability to the driver. At any point of dangerous conditions, indicated by successful comparison with said second State Definition, the constants denoting how steering ratio is to be reduced (such as speeds, gains, etc.) are provided to downstream control software, which then decreases steering ratio accordingly, through modulation of Variable-Ratio Drive 504. If, at any point, vehicle speed is significantly increased (which will be noted via block 210), new State Definitions will be created as described above, to reflect new circumstances.

Control of steering ratio is chosen in this application over vehicle speed, in that rapid deceleration is a formidable risk factor.

Figure 6:
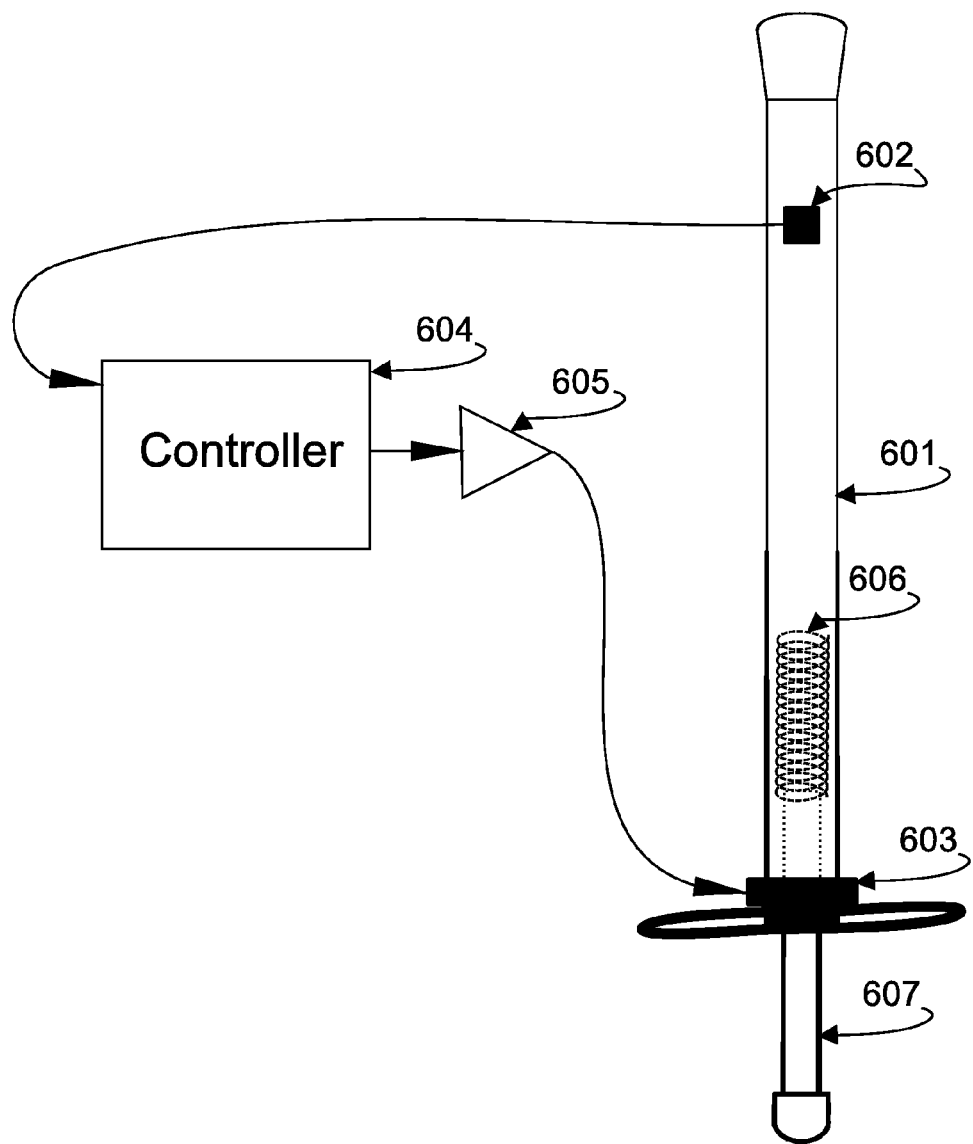
FIG. 6 shows a block diagram of an embodiment of the invention used to augment safety of a pogo stick.

Referring now to FIG. 6, three-axis Accelerometer 602 is affixed to Pogo Stick 601 at the nominal center of gravity of the stick when being ridden by an average user. Damper 603 is affixed to the lower portion of the outer tube of Pogo Stick 601, fully covering the inner tube when fully extended, below Spring 606. Damper 603 may employ magnetic-rheonetic or electro-rheonetic fluid, magnetic repulsion or attraction, and other methods through which resistance may be introduced between inner and outer tubes of Pogo Stick 601. Controller 604 receives as input accelerations in three axes from Accelerometer 602, and provides a control signal to Pulse width Modulator 605, which variable excites Damper 603. It can be seen that said control signal from Controller 604 therefore modulates Damper 606, variably reducing kinetic energy storage realizable from Spring 606. Controller 604 contains an embodiment of the current invention, as shown in FIG. 2, that context following:

Signal Acquisition 201 receives as input inclinations and accelerations in the sagittal, coronal, and transverse planes of the pogo stick, and hence the rider. Structural Model 203 contains dynamic behavior of the spring of the pogo stick and a rough human rider model consisting of an unknown mass, a first pair of spherical pivots, a first pair of unknown lengths, a pair of hinges, a second pair of unknown lengths, and a second pair of spherical pivots; representative of a human body center of mass, two hip joints, two femurs, two knees, two tibias, and two ankles, with nominal hip and knee spacing and ankle spacing matching that of the pogo stick. Model Resolver 204 continuously calculates rider mass, rider femur length, rider tibia length, rider knee angle, sagittal angle of rebound, coronal angle of rebound, and coefficient of friction between the end of the pogo stick and the ground. Sagittal and coronal rebound angles and tip coefficient of friction are provided with pogo stick inclinations and accelerations to History Buffer 205.

In operation, downstream control software continuously calculates deviation in the sagittal and coronal planes with each bounce, to ascertain rider ability to control the stick. This information, in addition to Stream 211, is provided to Criteria Selector 206. Event Indicator 210 provides a signal to Criteria Selector 206 and optionally State Criteria Buffer 207 at the beginning of each descent of the pogo stick, as indicated by Accelerometer 602 of FIG. 5. Upon receipt of said signal, Criteria Selector 206 inspects relative ability of the rider in both sagittal and coronal planes and modeled trajectory of the impending bounce, to choose the axis most likely to cause rider upset. Criteria Selector 206 then creates an unsafe State Definition comprised of safe trajectory limits of the impending bounce consistent with both rider ability and current conditions, storing this State Definition in State Criteria 207.

As the rider bounce continues, Comparator 208 indicates an unsafe state to State Condition Buffer 209 if said unsafe State Definition is met, causing State Condition Buffer 209 to supply damping control parameters (such as time constants or gains) to downstream control software, which then increases spring damping through variable activation of Damper 603 of FIG. 6, as described above.

Embodiments may include sufficient buffering such that a user need not activate switch 308 immediately but may instead rely on the buffering to allow the user to activate the switch within a threshold level of time (e.g., 5 seconds) since the event of interest occurred. Furthermore, embodiments such as FIG. 3 include three sensors however other embodiments may use a single sensor, two sensors, or more than three sensors depending on the movement or state to be monitored and the level of precision desired. For example, an embodiment may include sensors 309 and 303 but not sensor 302, thereby relying on accelerations but no positional information.

While embodiments regarding the knee are discussed at length, the application of embodiments described herein are also applied to golf carts and Pogo sticks. Thus, the embodiments may be broadly applied to other situations addressing various animal (e.g., human) joints (e.g., elbow, finger, toe, ankle, hip, shoulder, neck, wrist, back/spine). Stimulations systems may couple with braces or prostheses (e.g., replacement limbs) but are not limited thereto.

Embodiments may include a positional guidance system. For example, a user may wear a sleeve over his or her knee. The sleeve may pockets to hold sensors such as sensors 309, 303. Those pockets may be position-adjustable using a coupler such as Velcro. The pockets may fixedly couple to the sleeve to ensure the user wears the same sensors in the same locations over time.

From the previous discussion, it can be seen that state determination may be driven by reaction of a structure to excitation, as opposed to simplistic excitation qualification only. Resultantly, state structure of the controlling entity can more closely reflect the structure of the controlled environment, extending the action of control to encompass effects not readily measured. This distinction allows adaptive operation beyond previous experience, in that multiple sensory inputs, whether previously observed or not, may resultant in the occurrence of marked operational parameters. It furthermore can be seen that state differentiation may be improved through inclusion of state determination means capable of discovering system metrics with optimal dynamic range in the run-time environment, which may or may not be known during system design.

Given capability of the current invention to create state definitions to affect control of a system, it is implicit and anticipated that capability to delete state definitions as needed is as well included.

Although shown herein at use in very simple control system, broad use of the current invention is anticipated in state machine implementations, many of which are known to be more complex, such as hierarchical state structures. In addition to control of physical devices shown herein, advantageous use of the present invention in non-physical applications, such as data flow control, is as well anticipated.

The variability and extrapolation problems normally seen in fixed or adjustable template-driven control systems can be seen in the disclosure above to be ameliorated by the creation and use of terms reflective of system response to stimuli in the run-time setting. Resultantly, a system using the techniques described herein better reflects the structure being controlled, greatly improving overall system response.

Thus, in an embodiment measured physical conditions (e.g., accelerations) are applied to a physical model of the joint (e.g., 3D model) being protected. Vectored forces on the load-bearing elements of that joint are obtained. This modeled force information is then used to control when and/or how to stimulate the opposing muscle. In an embodiment, non-customized measurements (e.g., general measurements from one or more accelerometers) are taken and applied to a model to get the consequences in that particular user's joint. In contrast, conventional systems only cover using motion information to determine when to stimulate, not how. Conventional systems do not use modeled vectored internal forces to control stimulation. Also, conventional systems do not use measured conditions to modify the physical model being used.

Also, in one embodiment by pressing a button, the patient or provider alerts the device to remember what conditions (especially internal forces) caused something negative (e.g., pain, instability). This contrasts with conventional pre-determined positional templates.

In an embodiment, upon learning of things like laxity of the joint, such knowledge is applied to a physical model so stimulation offsets the (predicted) force on internal load-bearing surfaces. Control of conventional stimulation systems using positions, accelerations, and the like assumes a linear system (e.g., position or acceleration directly causes problems). This is overly simplistic for real world biological conditions, which have many compliances, resistances, and the like. For example, an arthritic joint has laxity that acts like hysteresis between two limits (when the condyles hit).

In an embodiment, data available (positions, accelerations, forces) when the patient pushes the button is used to find which data items in the current condition are most distinct from normal operation or other states. Values are used only for the most readily-visible data items (e.g., medial condyle force) and then only those values are monitored to flag that state is again occurring. This approach lets the controller find the most significant items to look for when monitoring for a specific condition (e.g., force on the joint). Thus an embodiment remembers a set of the most visible things to herald a state. Conventional systems looks at a list of data items (identities) that is pre-determined when the system is designed. Just like a pre-determined positional template, this is a pre-determined laundry list that is overly simplistic and not customized to the user and his or her current conditions (e.g., weight, activity).

An embodiment includes (a) modeling a first internal force applied to a model of a user's joint (e.g., knee) based on a first external force (e.g., positive acceleration) externally applied to the joint at a first position (e.g., from an inferior direction acting on the tibia); (b) modeling a second internal force applied to the model based on a second external force (e.g., deceleration) externally applied to the joint at a second position (from a superior direction acting on the femur) unequal to the first position; (c) comparing the first and second modeled internal forces (e.g., to determine if they are similar); and (d) stimulating the user based on the comparison (e.g., stimulating the user because the second external force, which may have been unknown, resulted in an internal force similar to a previous internal force that was marked as being problematic). Thus an embodiment may be able to identify an internal force as being problematic despite never having "seen" the position that indirectly generates the problematic internal force.

An embodiment may include receiving input from the user corresponding to the first external source (e.g., activation of a switch when the user feels pain); and modeling the first internal force based on receiving the input.

An embodiment may include dynamically creating new models (e.g., on the fly and after the system is out in the field with the patient) based on receiving the input from the user substantially contemporaneously with the user experiencing one of joint pain and joint instability (e.g., existing or occurring in the same period of time such as within 5 or 10 seconds of the user feeling pain).

An embodiment includes determining the first and second modeled internal forces are substantially equal according to a chosen factor (e.g., magnitude, vector, and point of application to the modeled joint, a highest derivative value of data, statistical prevalence, and the like); and stimulating the user based on the determination.

An embodiment may also include determining a first characteristic corresponding to the first internal force; and determining a second plurality of characteristics corresponding to the second internal force; wherein comparing the first and second modeled internal forces includes comparing the first characteristic and the second characteristic, the second characteristic being included in the plurality of characteristics. For example, if the user marks a pain event and one element out of fifteen appears significant (e.g., an outlier or statistically prevalent value) then the significant factor may be used for later comparisons to identify that pain state. As another example, one may not appreciate what factor will be most significant in determining a problematic state exists until after the product is in the field. Thus, the ability to evaluate several factors and choose among them to build states on those significant factors can help build predictive models long after a device is released to the field.

Figure 7:
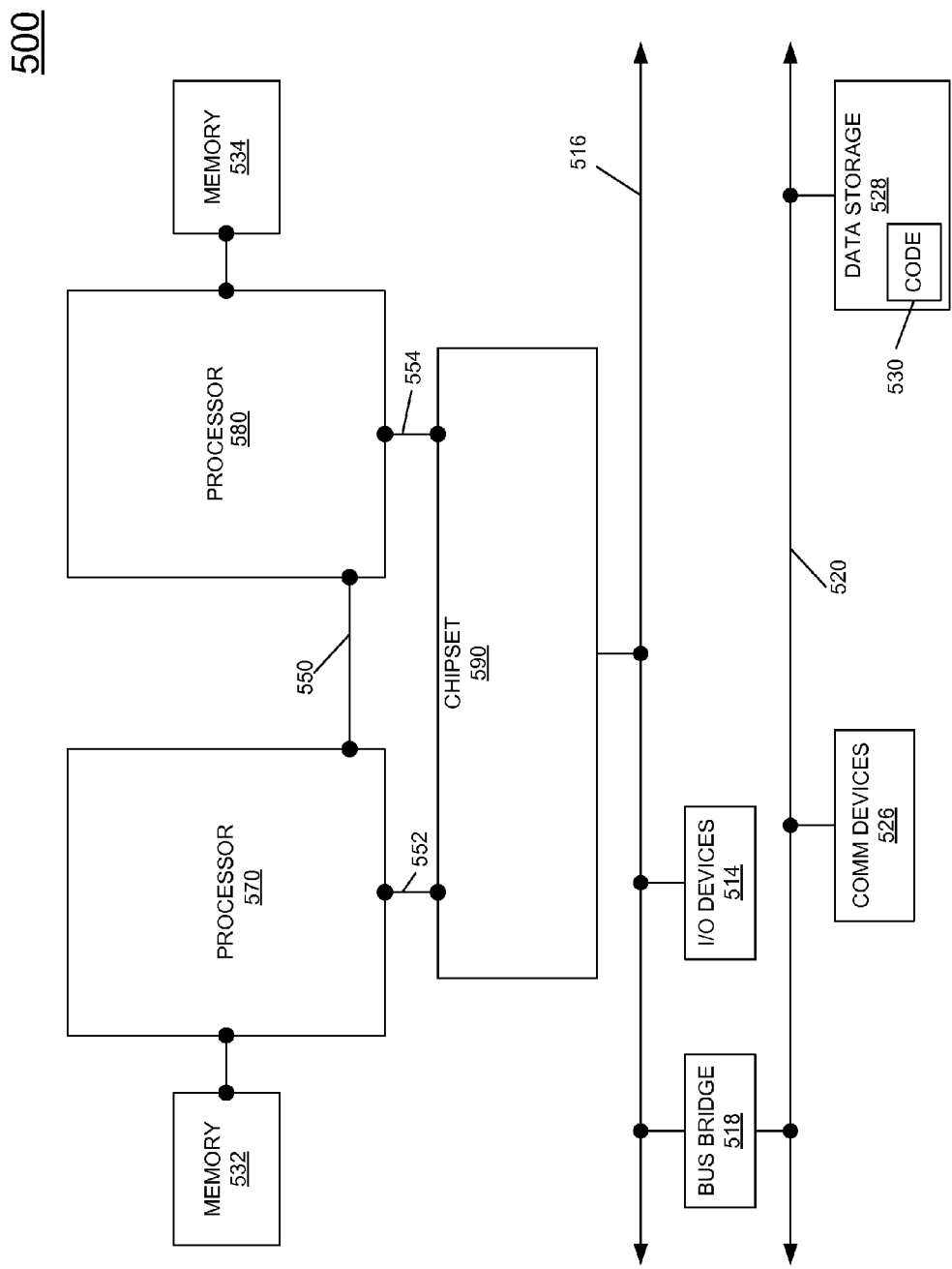
FIG. 7 includes a block diagram of a system for use with embodiments of the invention.

Embodiments may be implemented in many different system types. Referring now to FIG. 7, shown is a block diagram of a system in accordance with an embodiment of the present invention. Multiprocessor system 500 is a point-to-point interconnect system, and includes a first processor 570 and a second processor 580 coupled via a point-to-point interconnect 550. Each of processors 570 and 580 may be multicore processors. The term "processor" may refer to any device or portion of a device that processes electronic data from registers and/or memory to transform that electronic data into other electronic data that may be stored in registers and/or memory. First processor 570 may include a memory controller hub (MCH) and point-to-point (P-P) interfaces. Similarly, second processor 580 may include a MCH and P-P interfaces. The MCHs may couple the processors to respective memories, namely memory 532 and memory 534, which may be portions of main memory (e.g., a dynamic random access memory (DRAM)) locally attached to the respective processors. First processor 570 and second processor 580 may be coupled to a chipset 590 via P-P interconnects, respectively. Chipset 590 may include P-P interfaces. Furthermore, chipset 590 may be coupled to a first bus 516 via an interface. Various input/output (I/O) devices 514 may be coupled to first bus 516, along with a bus bridge 518, which couples first bus 516 to a second bus 520. Various devices may be coupled to second bus 520 including, for example, communication devices 526, and data storage unit 528 such as a disk drive or other mass storage device, which may include code 530, in one embodiment.

Embodiments may be implemented in code and may be stored on a non-transitory storage medium having stored thereon instructions which can be used to program a system to perform the instructions. The storage medium may include, but is not limited to, any type of disk including floppy disks, optical disks, optical disks, solid state drives (SSDs), compact disk read-only memories (CD-ROMs), compact disk rewritables (CD-RWs), and magneto-optical disks, semiconductor devices such as read-only memories (ROMs), random access memories (RAMs) such as dynamic random access memories (DRAMs), static random access memories (SRAMs), erasable programmable read-only memories (EPROMs), flash memories, electrically erasable programmable read-only memories (EEPROMs), magnetic or optical cards, or any other type of media suitable for storing electronic instructions. Embodiments of the invention may be described herein with reference to data such as instructions, functions, procedures, data structures, application programs, configuration settings, code, and the like. When the data is accessed by a machine, the machine may respond by performing tasks, defining abstract data types, establishing low-level hardware contexts, and/or performing other operations, as described in greater detail herein. The data may be stored in volatile and/or non-volatile data storage. The terms "code" or "program" cover a broad range of components and constructs, including applications, drivers, processes, routines, methods, modules, and subprograms and may refer to any collection of instructions which, when executed by a processing system, performs a desired operation or operations. In addition, alternative embodiments may include processes that use fewer than all of the disclosed operations, processes that use additional operations, processes that use the same operations in a different sequence, and processes in which the individual operations disclosed herein are combined, subdivided, or otherwise altered. Components or modules may be combined or separated as desired, and may be positioned in one or more portions of a device.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A system comprising:
    at least one memory;
    an electrode;
    at least one sensor comprising at least member selected from the group comprising: at least one electrode, at least one accelerometer, and a positional angular sensor;
    at least one signal conditioner including a frequency filter and an analog-to-digital (A/D) converter;
    a comparator;
    at least one processor, coupled to the at least one memory, to perform steps comprising:
        (a)(i) measurement of a first movement or position of a limb attached to a user's joint via the at least one sensor;
        (a)(ii) measurement of a second movement or position of the limb attached to the joint via the at least one sensor;
        (a)(iii) condition the measurement of the first movement or position of the limb via the as least one signal conditioner;
        (a)(iv) condition the measurement of the second movement or position of the limb via the at least one signal conditioner;
    at least one finite state controller, coupled to the at least one memory, to perform steps comprising:
        (b)(i) model a first internal force applied to the user's joint based on the conditioned measurement of the first movement or position of the limb attached to the joint at a first point in time;
        (b)(ii) model a second internal force applied to the joint based on the conditioned measurement of the second movement or position of the limb attached to the joint at a second point in time;
    wherein the at least one processor is to further perform steps comprising:
        (c)(1) compare, via the comparator, the first and the second modeled internal forces; and
        (c)(2) stimulate muscle of the user, via the electrode, based on the comparison.

2. The system of claim 1, wherein the at least one processor is to:
    receive input from the user corresponding to the first movement or position; and
    store the first internal force based on receiving the input.

3. The system of claim 2, wherein receiving the input from the user is substantially contemporaneous with the user experiencing one of joint pain and joint instability.

4. The system of claim 1, wherein at least one of the at least one finite state controller and the at least one processor is to:
    determine a second plurality of characteristics corresponding to the first modeled internal force;
    determine a first characteristic that is statistically significant, the first characteristic included in the plurality of characteristics;
    determine a second plurality of characteristics corresponding to the second modeled internal force; and
    compare the first and second modeled internal forces based on comparison of the first characteristic and a second characteristic, the second characteristic being included in the second plurality of characteristics.

5. The system of claim 4, wherein the first characteristic corresponds to the first internal force.

6. The system of claim 4, wherein one or more of the first and second characteristics is historical.

* * * * *

UNITED STATES PATENT AND TRADEMARK OFFICE
CERTIFICATE OF CORRECTION

PATENT NO. : 9,734,296 B2
APPLICATION NO. : 13/878586
DATED : August 15, 2017
INVENTOR(S) : Larry J. Kirn Page 1 of 1

It is certified that error appears in the above-identified patent and that said Letters Patent is hereby corrected as shown below:

In the Claims

Claim 1, Line 48, "via the as least" should be --via the at least--.

Claim 4, Line 33, "determine a second plurality" should be --determine a plurality--.

Signed and Sealed this
Twelfth Day of December, 2017

Joseph Matal
*Performing the Functions and Duties of the
Under Secretary of Commerce for Intellectual Property and
Director of the United States Patent and Trademark Office*